United States Patent
Wing et al.

(10) Patent No.: US 8,911,442 B2
(45) Date of Patent: Dec. 16, 2014

(54) SYSTEMS FOR VERTEBRAL ADJUSTMENTS AND ROD REDUCTION

(75) Inventors: Jon Wing, Crystal Lake, IL (US); Clark Hutton, Oceanside, CA (US); Garrett Gleeson, Encinitas, CA (US); Per Freitag, Springfield, IL (US)

(73) Assignee: Alphatec Spine, Inc., Carlsbad, CA (US)

(*) Notice: Subject to any disclaimer, the term of this patent is extended or adjusted under 35 U.S.C. 154(b) by 473 days.

(21) Appl. No.: 13/282,248

(22) Filed: Oct. 26, 2011

(65) Prior Publication Data

US 2013/0110184 A1 May 2, 2013

(51) Int. Cl.
*A61B 17/70* (2006.01)
(52) U.S. Cl.
CPC ........... *A61B 17/7085* (2013.01); *A61B 17/708* (2013.01); *A61B 17/7001* (2013.01)
USPC .......................................... 606/86 A; 606/90
(58) Field of Classification Search
USPC ............................ 606/86 A, 86 R, 99, 105, 90
See application file for complete search history.

(56) References Cited

U.S. PATENT DOCUMENTS

| | | | |
|---|---|---|---|
| 2005/0245928 A1* | 11/2005 | Colleran et al. | 606/61 |
| 2008/0077155 A1* | 3/2008 | Diederich et al. | 606/105 |
| 2010/0036443 A1* | 2/2010 | Hutton et al. | 606/86 R |
| 2010/0069972 A1* | 3/2010 | Jones et al. | 606/86 A |
| 2010/0114179 A1* | 5/2010 | Moore et al. | 606/308 |

* cited by examiner

*Primary Examiner* — Eduardo C Robert
*Assistant Examiner* — Julianna N Harvey
(74) *Attorney, Agent, or Firm* — Michael J. Loi

(57) ABSTRACT

An instrument for compression and distraction of a vertebral segment and reducing a surgical rod includes a first arm, a second arm, a coupler, and a reducer. The first arm includes a first aperture for receiving a first screw extender that attaches to a first vertebra. The second arm pivotably couples to the first arm and includes a second aperture for receiving a second screw extender that attaches to a second vertebra. The coupler links the first arm to the second arm to position the first arm relative to the second arm for compression and distraction of the first vertebra relative to the second vertebra. The reducer is received within the second aperture for reducing a surgical rod within the second screw extender.

10 Claims, 8 Drawing Sheets

SYSTEMS FOR VERTEBRAL ADJUSTMENTS AND ROD REDUCTION

FIELD

The present invention relates generally to the field of surgery, and more specifically, to systems for compression and distraction of vertebral segments and reduction of surgical rods.

BACKGROUND

Spondylolisthesis is a condition in which a bone (vertebra) in the lower part of the spine slips out of the proper position onto the bone below it. For example, one vertebra may be properly aligned with the spinal column and another adjacent vertebra may be misaligned and slipped over the aligned vertebra. In children, spondylolisthesis usually occurs between the fifth bone in the lower back (lumbar vertebra) and the first bone in the sacrum (pelvis) area. It is often due to a birth defect in that area of the spine (such as spondylolysis) or sudden injury (acute trauma). In adults, the most common cause is degenerative disease (such as arthritis or spondylosis). The slip usually occurs between the fourth and fifth lumbar vertebrae.

Other causes of spondylolisthesis include bone diseases, traumatic fractures, and stress fractures (commonly seen in gymnasts). Certain sport activities, such as gymnastics, weight lifting, and football, put a great deal of stress on the bones in the lower back. They also require that the athlete constantly overstretch (hyperextend) the spine. This can lead to a stress fracture on one or both sides of the vertebra. A stress fracture can cause a spinal bone to become weak and shift out of place.

One form of treatment for spondylolisthesis involves inserting a system of pedicle screws with rod-receiving polyaxial heads that receive rigid rods to link two or more vertebrae. Typically, the screws may be inserted into the pedicles of two adjacent vertebrae during surgery. Screw extenders may be attached to the polyaxial heads of the screws to facilitate insertion of the surgical rods and provide leverage that increases torque for aligning the spine. The screw extenders may include substantially tubular bodies of a uniform diameter. A surgical rod may then be placed in line with the spine and coupled to one of the screws attached to the aligned vertebra. In order to properly align the slipped vertebra, the surgical rod must be coupled to a screw attached to the slipped vertebra. Typically, an instrument known as a rod reducer may be used to "reduce" the surgical rod into the polyaxial head. Alternatively, the rod reducer may grasp the polyaxial head and "pull" the polyaxial head onto the surgical rod. Once the surgical rod has been coupled to both polyaxial heads, setscrews may be inserted to lock the rod in place.

At times, it may be desirable to also compress or distract the two vertebrae as well in order to maneuver various portions of one vertebra away from the other. Compression or distraction may be necessary to increase or decrease the interdiscal space between the adjacent vertebrae. This may be necessary for various reasons: relief from slipped or herniated discs, spacing for pinched nerves, and/or insertion of supportive interbody spacers and bone grafts for bone fusion. Typically, an instrument known as a compressor-distractor may be used to compress and distract the two vertebrae.

Thus, during the surgical procedure, one instrument must be used to reduce the rod into the screw head to align the vertebrae and another instrument must be sued to compress and/or distract the vertebrae using the screw extenders. Such procedures may require a surgeon to frequently alternate between the various instruments. For example, a compressor-distractor instrument may be coupled to the screw extenders to compress and distract two or more vertebrae. After compression and/or distraction, the surgeon may use a rod reducer instrument to reduce the rod into the screw head until the rod is properly seated. Frequent switching back and forth between these instruments increases surgery times and increases the chance for error on the part of the surgeon. Therefore, it would be desirable to have an instrument that performs multiple functions on the screw extenders and vertebral segments.

SUMMARY

An instrument for compression and distraction of a vertebral segment and reducing a surgical rod includes a first arm, a second arm, a coupler, and a reducer. The first arm includes a first aperture for receiving a first screw extender that attaches to a first vertebra. The second arm pivotably couples to the first arm and includes a second aperture for receiving a second screw extender that attaches to a second vertebra. The coupler links the first arm to the second arm to position the first arm relative to the second arm for compression and distraction of the first vertebra relative to the second vertebra. The reducer is received within the second aperture for reducing a surgical rod within the second screw extender.

In other features, the first aperture includes a first diameter and the second aperture includes a second diameter greater than the first diameter. The instrument further includes a pivot pin that links proximal ends of the first arm and the second arm. The instrument further includes coupler apertures in distal ends of the first arm and the second arm for receiving the coupler. The coupler includes a first thread for engagement with the first arm and a second thread for engagement with the second arm. The instrument further includes pivot collars within distal ends of the first and second arms for pivotally linking the coupler with the first arm and the second arm.

A system for one or more surgical procedures includes a first arm, a second arm, a removable sleeve in a first configuration, and a reducer in a second configuration. The first arm includes a first aperture for coupling with a first screw extender that attaches to a first vertebra. The second arm pivotably couples to the first arm and includes a second aperture having a first configuration and a second configuration. The removable sleeve engages the second aperture in the first configuration for coupling with a second screw extender that attaches to a second vertebra. The reducer engages the second aperture in the second configuration to reduce a surgical rod within the second screw extender. The coupler positions the first arm relative to the second arm for compression and distraction of the first vertebra relative to the second vertebra in the first and second configurations.

In other features, the first aperture includes a first diameter and the second aperture includes a second diameter greater than the first diameter. The system further includes a pivot pin that links proximal ends of the first arm and the second arm. The system further includes coupler apertures in distal ends of the first arm and the second arm for receiving the coupler. The coupler includes a first thread for engagement with the first arm and a second thread for engagement with the second arm. The system further includes rotatable links within distal ends of the first and second arms for rotatably coupling the coupler with the first arm and the second arm.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The exemplary embodiments of the present invention include an instrument and system for compression and distraction of a vertebral segment and reduction of a surgical rod. The instrument includes a first arm, a second arm pivotably coupled to the first arm, a reducer, and a coupler. The first arm includes a first aperture for receiving a first screw extender that attaches to a first vertebra. The second arm includes a second aperture having a first configuration for receiving a second screw extender that attaches to a second vertebra and second configuration. The reducer is received within the second aperture in the second configuration for reducing a surgical rod within the second screw extender. The coupler positions the first arm relative to the second arm for compression and distraction of the first and second vertebrae. In some instances, it may be desirable for the instrument to function solely as a compressor-distractor. The system for compression, distraction, and reduction may include the instrument and a sleeve and have two configurations. In a first configuration, the system may include the arms, coupler, and reducer to form the instrument. In a second configuration, the system may include the arms, coupler, and the sleeve to form a compressor-distractor instrument.

The exemplary embodiments of the present invention are advantageous over the prior art because the instrument and system may reduce the number of instances in which a surgeon must switch between instruments during a surgical procedure. This reduction may decrease surgical times, improve the accuracy of the surgeon, and provide greater flexibility for compression/distraction and reduction procedures through integration of multiple instruments into one instrument.

Figure 1:
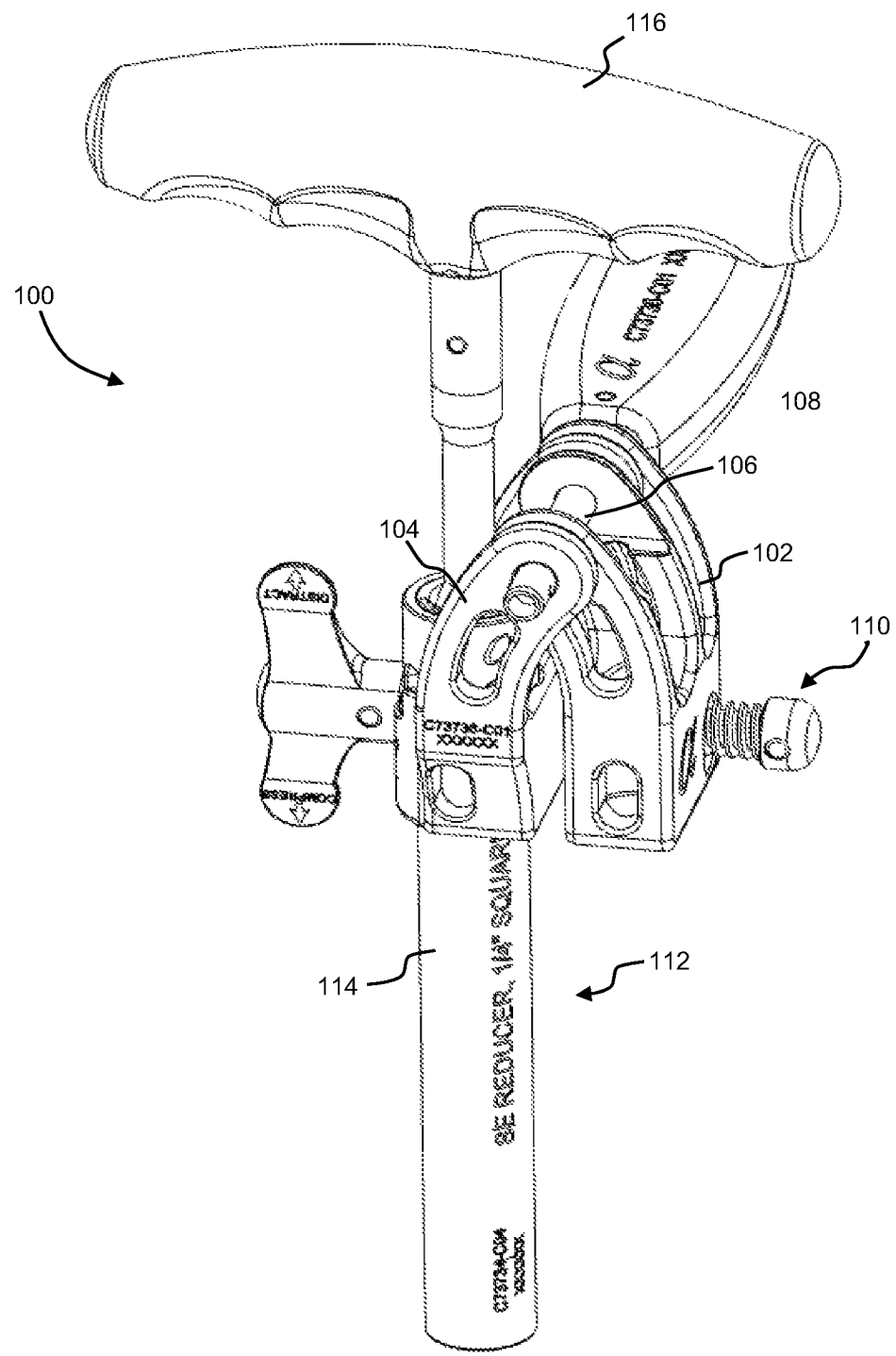
FIG. 1 is a perspective view of an exemplary instrument for compression, distraction, and reduction procedures according to the principles of the present disclosure.

Referring now to FIG. 1, an instrument 100 for compression and distraction of a vertebral segment and reducing a surgical rod is shown. A first arm 102 is configured to receive and couple with a first screw extender that attaches to a first vertebra. A second arm 104 pivotably couples to the first arm 102, for example by a pin 106, and is configured to receive a second screw extender that attaches to a second adjacent vertebra. A handle 108 may couple with the pin 106 for gripping during surgery. Both the pin 106 and the handle 108 may be removable for easy sterilization and cleaning. A coupler 110 links the first arm 102 to the second arm 104 to position the first arm 102 relative to the second arm 104 for compression and distraction of the first vertebra relative to the second vertebra. The second arm 104 may also receive a reducer 112 for reducing a surgical rod within the second screw extender. The reducer 112 may include a reduction tube 114 and an actuator 116. The instrument 100 allows a surgeon to use a single instrument to couple with a pair of screw extenders on adjacent vertebrae and compress, distract, and reduce a spinal rod as discussed herein.

Figure 2:
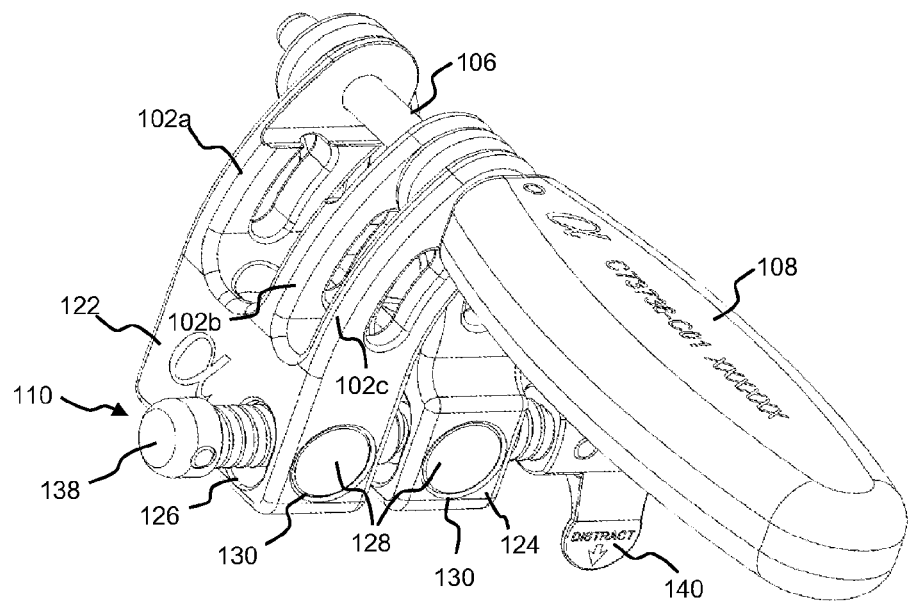
FIG. 2 is a perspective view of a compressor-distractor of the instrument according to the principles of the present disclosure.
Figure 3:
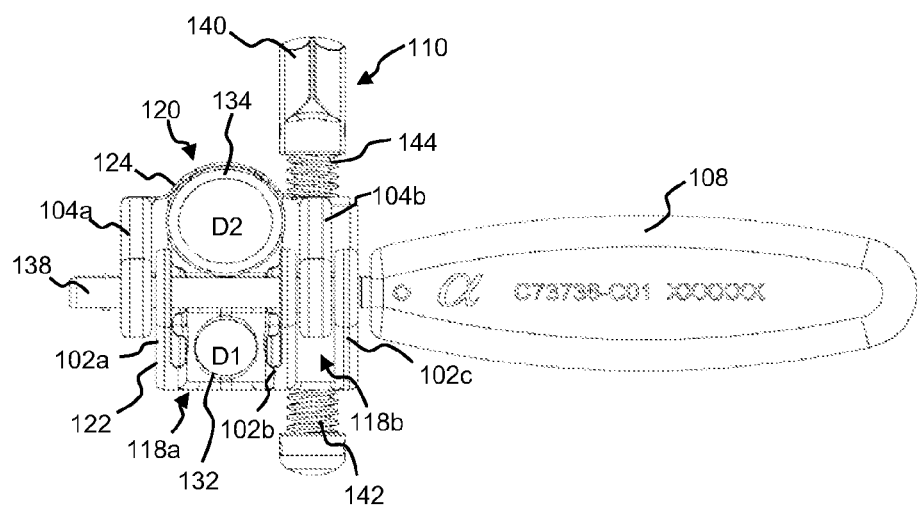
FIG. 3 is an elevational top view of the compressor-distractor of FIG. 2 according to the principles of the present disclosure.

Referring also now to FIGS. 2 and 3, the first arm 102 and the second arm 104 include proximal ends that may be configured to curve toward each other forming an arched or "A" shaped configuration. Each arm 102 and 104 may be slotted to permit linkage at their proximal ends by the pin 106 and passage of additional instruments through various apertures, bores, and openings in their distal ends. For example, the first arm 102 may be separated into three sections 102a, 102b, and 102c by two slots 118a and 118b. The second arm 104 may be separated into two sections 104a and 104b by one slot 120. Thus, the proximal ends of the first arm 102 and second arm 104 may cross or intersect similar to the fingers on a pair of clasped hands.

The distal ends of the first arm 102 and second arm 104 include base portions for receiving the coupler 110, extenders, and other instruments. For example, the distal end of the first arm 102 includes a first base portion 122 and the distal end of the second arm 104 includes a second base portion 124. Each base portion 122 and 124 is configured for receiving at least one of the screw extenders, the coupler 110, and the reduction tube 114. Each of the base portions 122 and 124 includes a coupler opening 126 though which the coupler 110 extends. The coupler openings 126 may be elliptical in shape to enable ends of the coupler 110 to exit the base portions 122 and 124 at various angles as the arms 102 and 104 pivot about the pin 106. Within the coupler openings 126, pivot collars 128 may receive the coupler 110 inside the base portions 122 and 124. The pivot collars 128 may pivot or rotate within pivot openings 130 intersecting the coupler openings 126. The pivot collars 128 enable the coupler 110 to pivot or rotate some degree as the arms 102 and 104 rotate about the pin 106.

Continuing with FIG. 3, the first base portion 122 includes a first aperture 132. For example, the first aperture 132 may be disposed between the sections 102a and 102b of the first arm 102. The first aperture 132 includes a first diameter D1. The second base portion 124 includes a second aperture 134. For example, the second aperture 134 may be disposed between the sections 104a and 104b of the second arm 104. The second aperture 134 includes a second diameter D2 that is greater than D1. The apertures 132 and 134 may be configured to receive screw extenders and/or other instruments and components as described herein.

Figure 13:
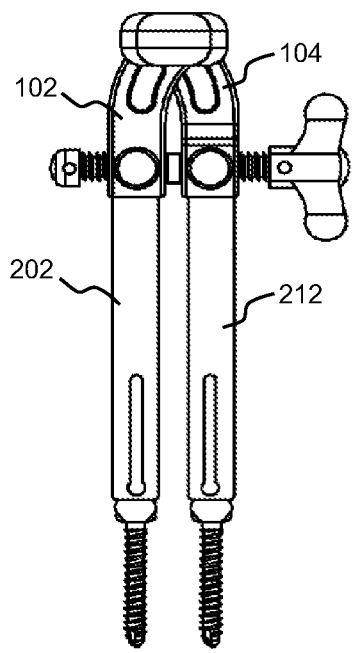
FIG. 13 illustrates the system of FIG. 12 in a compressed state.
Figure 14:
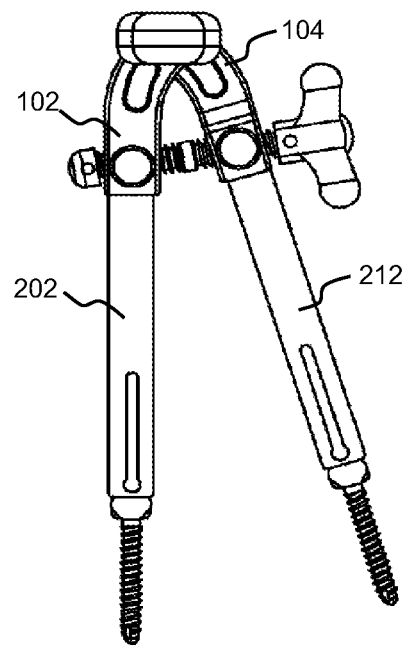
FIG. 14 illustrates the system of FIG. 12 in a distracted state.

The first arm 102 and the second arm 104 may be linked at their distal ends by the coupler 110 to enable translation of the distal ends. For example, the distal ends may extend parallel to one another in a first position and translate away from each other to a second position as illustrated in FIGS. 13 and 14. The coupler 110 includes a shaft 138 that extends though coupler apertures 126 in the distal ends of the arms 102 and 104. The shaft 138 may include one or more threaded sections that spread and collapse the first arm 102 and the second arm 104 depending on the turning direction of knob 140. For example in FIG. 3, the shaft 138 includes a first thread 142 for engagement with the first arm 102 and a second thread 144 for engagement with the second arm 104.

Figure 4:
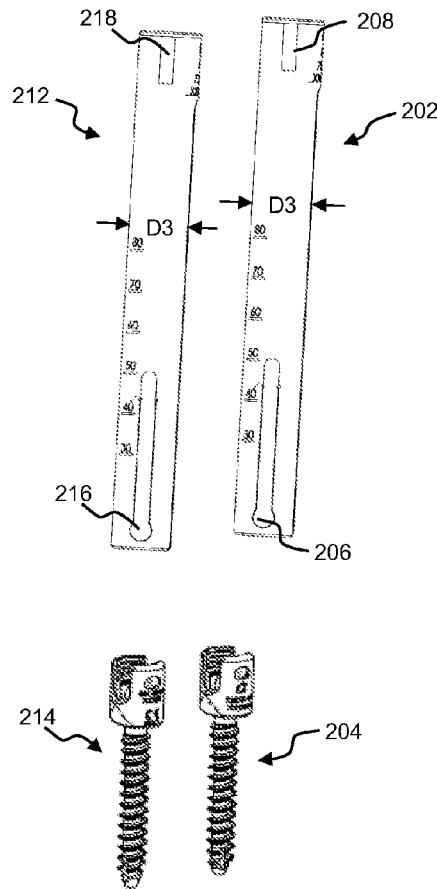
FIG. 4 is a perspective view of a pair of polyaxial pedicle screws and associated screw extenders.

Referring now also to FIG. 4, the first aperture 132 may be configured to receive a first screw extender 202 that attaches to a first polyaxial screw 204. For example, the first extender 202 may include a substantially circular cross-section having an outer diameter D3 corresponding to the first diameter D1 of the first aperture 132. At its distal end, various attachment features 206 may be used to rigidly secure the first extender 202 to the polyaxial head of the first screw 204. For example, the attachment features 206 may include elastically flexible tabs that mate with pockets or other features on the screw 204. At its proximal end, various coupling features 208 may be used to couple with mating features in the first aperture 132. For example, the coupling features 208 may include slots in the proximal end for receiving a mating projection (not shown) on the first aperture 132. The coupling features 208 may prevent the first extender 202 from passing completely through the first aperture 132.

The second aperture 134 may be configured to receive a second screw extender 212 that attaches to a second polyaxial screw 214. The second extender 212 may be substantially similar to the first extender 202 having an outer diameter D3 corresponding to the first diameter D1. For example, the second extender 212 may also include a substantially circular cross-section having an outer diameter D3 corresponding to the first diameter D1 of the first aperture 132. At its distal end, various attachment features 216, such as flexible tabs, may be used to rigidly secure the second extender 212 to the polyaxial head of the second screw 214. At its proximal end, various coupling features 218, such as slots, may be used to couple with mating features of the reducer 112 or other devices described herein and similar to mating projections of the first aperture 132.

Figure 5:
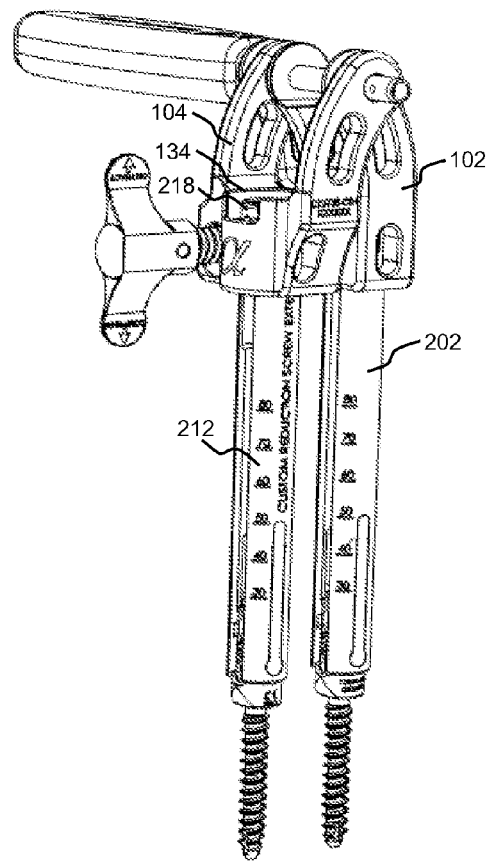
FIG. 5 is a perspective view of the compressor-distractor of FIGS. 2 and 3 engaged with the screw extenders of FIG. 4.

In FIG. 5, the arms 102 and 104 may be placed onto the proximal ends of the extenders 202 and 212. The first aperture 132 may include various coupling features to attach and/or releasably couple with the features 208 of the first extender 202 such as a projection (not shown) extending radially inward from an inner surface of the first aperture 132. The second aperture 134 may surround the proximal end of the second extender 212. However, the diameter D2 of the second aperture 144 is greater than the outer diameter D3 of the second extender 212. Thus, the second aperture 134 may not attach and/or releasably couple with the coupling features 218 of the second extender 212.

Figure 7:
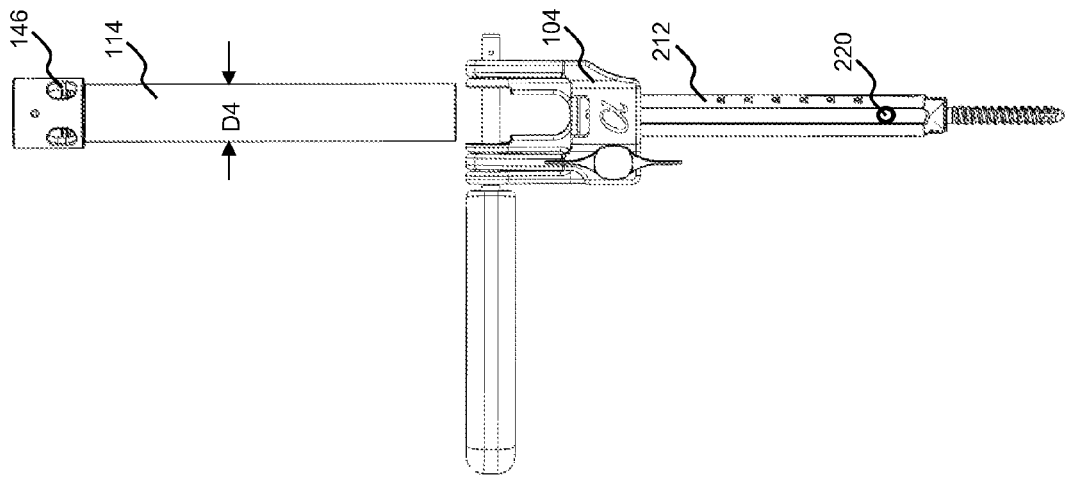
FIG. 7 is an elevational side view showing a reduction tube of the instrument advancing through the compressor-distractor according to the principles of the present disclosure.
Figure 6:
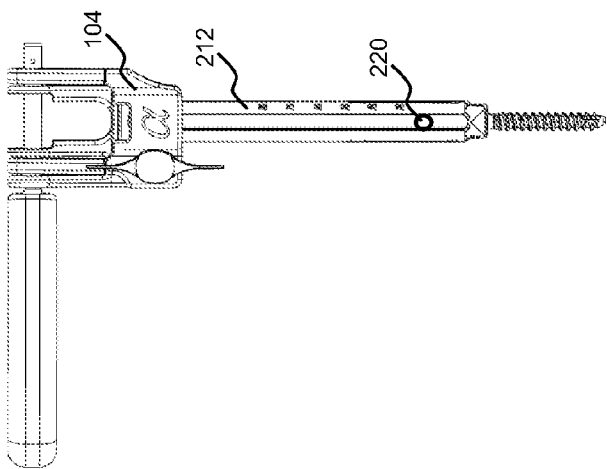
FIG. 6 is an elevational side view of the compressor-distractor engaging the screw extenders as illustrated in FIG. 5.

Continuing now also with FIGS. 6-9, the reducer 112 of FIG. 1 may be inserted over the second extender 212 to enable compression and distraction of the first extender 202 relative to the second extender 212 as well as reduction of a surgical rod 220 disposed within the second extender 212. In FIG. 6, the first arm 102 (hidden behind the second arm 104) and the second arm 104 are situated over the proximal ends of the first extender 202 (hidden behind the second extender 212) and the second extender 212. The first aperture 132 may be coupled or attached to the proximal end of the first extender 202 as described above with reference to FIG. 5. In FIG. 7, the reduction tube 114 of the reducer 112 may be inserted through the proximal opening of the second aperture 134.

The reduction tube 114 may include a threaded portion that rotates freely within the proximal end of the reduction tube 114. The threaded portion engages a mating inner thread on the proximal end of the second extender 212. As the threaded portion rotates within the proximal end of the reduction tube 114, the second extender 212 may move distally or proximally relative to the reduction tube 114. The reduction tube 114 includes an outer diameter D4 corresponding to the diameter D2 of the second aperture 134 and an inner diameter corresponding to the diameter D3 of the second extender 212. The reduction tube 114 and second aperture 134 may include various coupling features to enable secure coupling therebetween. For example, the proximal end of the reduction tube 114 may include coupling features 146, such as openings, slots, and the like for coupling within the aperture 134. An exemplary reduction tube may be found in U.S. Pub. No. 2010/0036443 incorporated by reference herein in its entirety.

Figure 9:
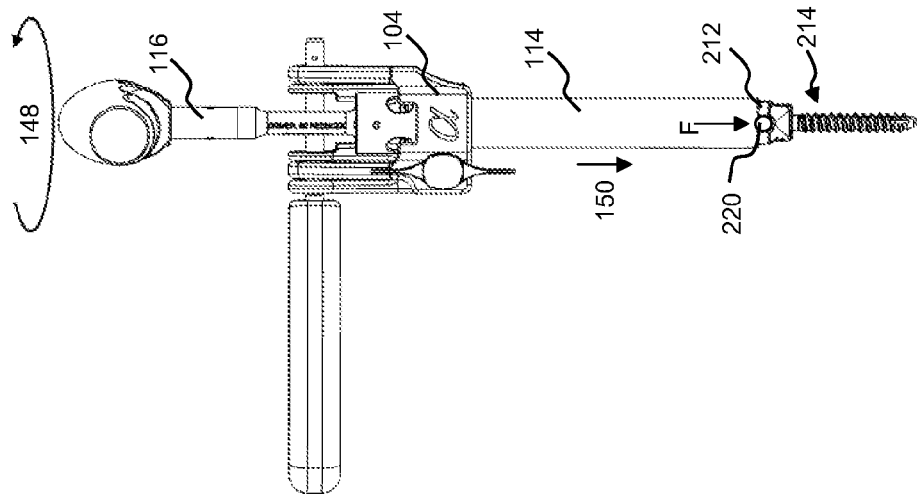
FIG. 9 is an elevational side view showing reduction of a rod within one of the screw extenders according to the principles of the present disclosure.
Figure 8:
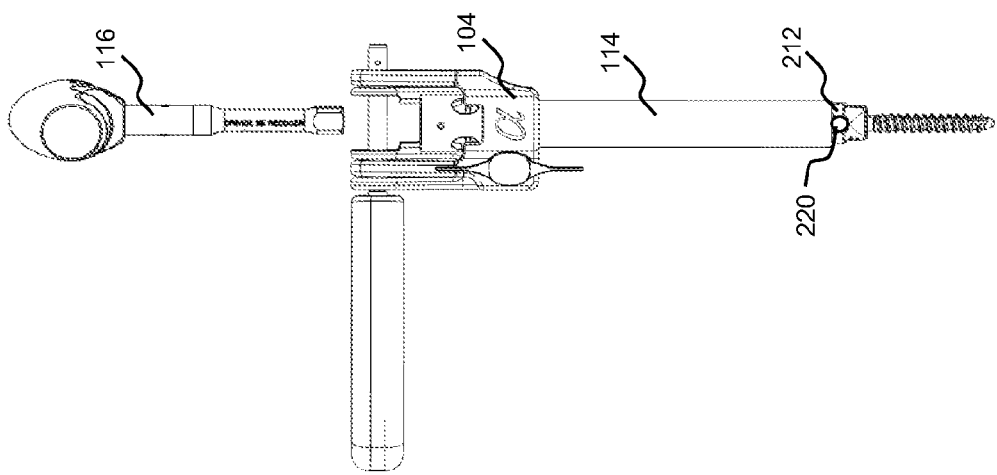
FIG. 8 is an elevational side view showing a handle prior to engagement with the reduction tube of FIG. 7.

Referring now to FIGS. 8 and 9, after insertion of the reduction tube 114, the actuator 116 may be inserted into the proximal end of the reduction tube 114. The reduction tube 114 and actuator 116 may be inserted simultaneously. As the actuator 116 rotates, as indicated by arrow 148, the reduction tube 114 may move distally towards the screw 214, as indicated by arrow 150. The reduction tube 114 may apply force F to the surgical rod 220 to reduce the rod 220 into the polyaxial head of the second screw 214. In other examples, the reduction tube 114 may apply force to the proximal end of the second extender 212 via the threaded engagement that pulls the second screw 214 towards the rod 220 to fully seat the rod 220 within the polyaxial head of the second screw 214.

Figure 10:
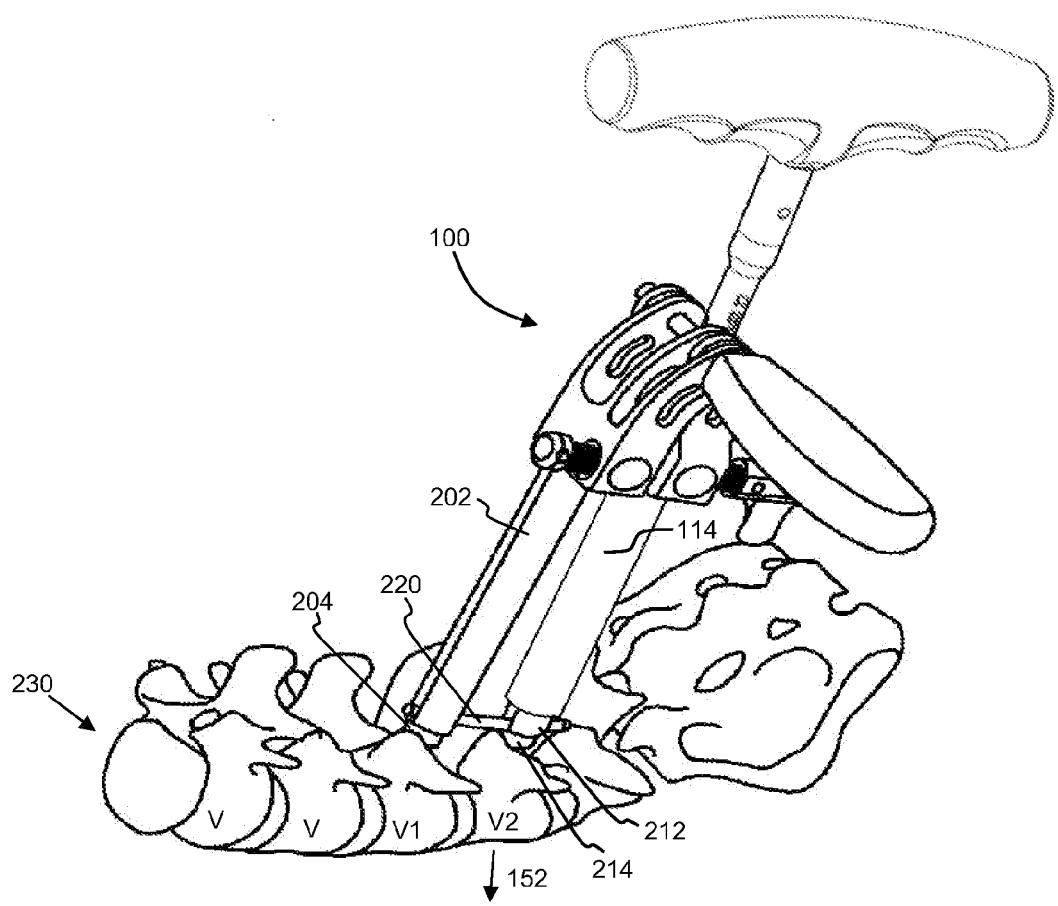
FIG. 10 is a perspective view of the instrument engaging screw extenders coupled with pedicle screws that are attached to vertebrae of a spinal column.
Figure 11:
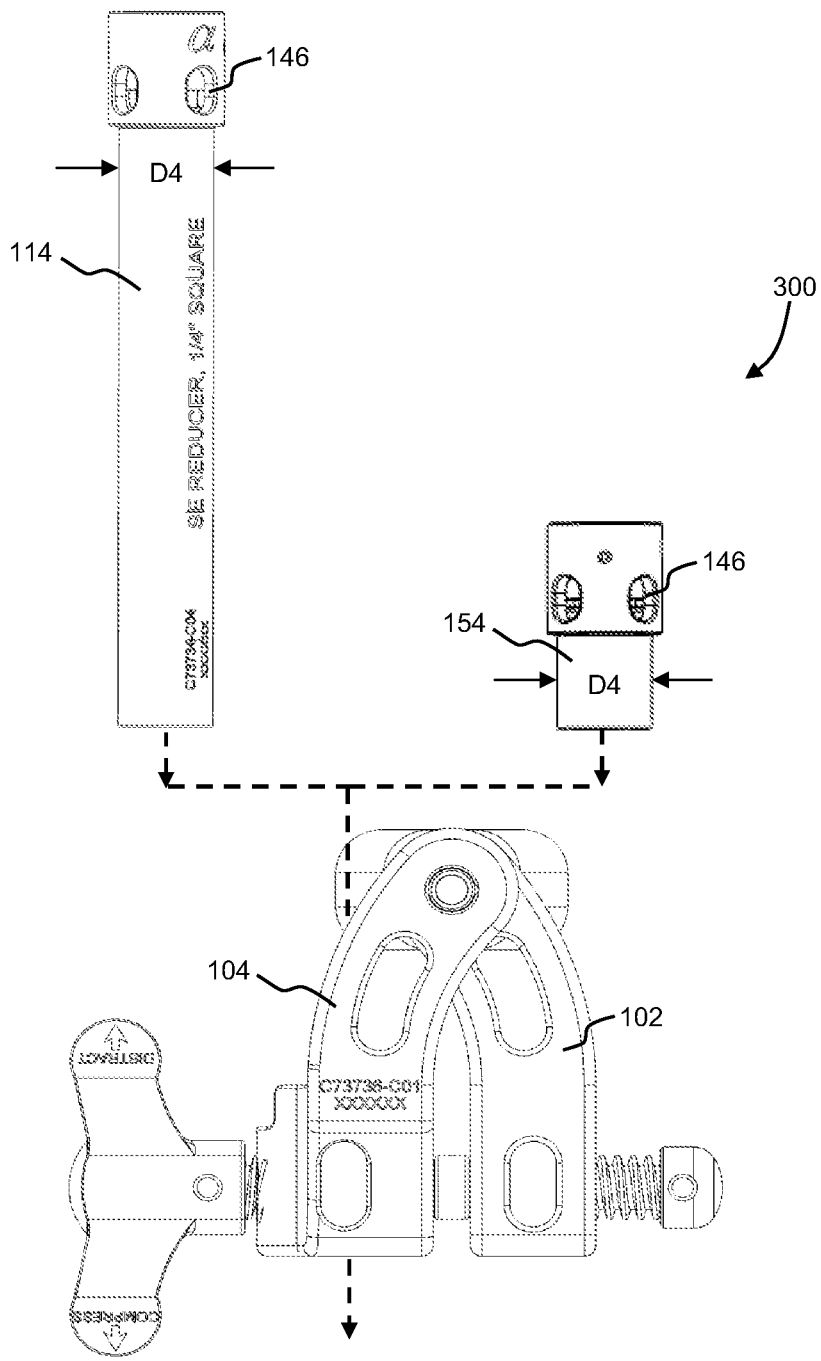
FIG. 11 illustrates a system comprising the compressor-distractor, the reduction tube, and a sleeve configurable between at least two configurations according to the principles of the present disclosure.

In FIG. 10, the screws 204 and 214 of FIG. 4 have been inserted into vertebrae V of a spinal column 212. The first screw 204, for example, may be inserted into a first vertebra V1 that is substantially aligned with the other vertebrae V of a spinal column 230. The second screw 214 may be inserted into a second vertebra V2 that has slipped forward of the first vertebra V1 in the anterior direction indicated by arrow 152. The extenders 202 and 212 are subsequently attached to the first and second screws 204 and 214 respectively, and the rod 220 may be inserted through the extenders 202 and 212. Once the screw extenders 202 and 212 have been attached to the screws 204 and 214, the instrument 100 may be attached as describe above with reference to FIGS. 6-9. The first aperture 132 may slide over the proximal end of the first extender 202 and the second aperture 144 may slide over the proximal end of the second extender 212. For example, the extenders 202 and 212 may enter through distal openings of the apertures 132 and 134 respectively. The reducer 114 may then slide over the proximal end of the second extender 212. For example, the reducer 114 may enter through a proximal end of the second aperture 134 and slide over the proximal end of the second extender 212.

In some instances, it may be desirable to use the instrument 100 without the reducer 112 for simpler compression and distraction procedures. For example, a surgeon may not require reduction of a rod to a polyaxial head of a screw. In such instances, a system 300 provides added versatility by providing the instrument 100 described above with the option of two configurations using one of the reduction tube 114 and a sleeve 154. The system 300 may be configured as either a compressor-distractor-reducer in a first configuration as described above with reference to the instrument 100 or as a compressor-distractor in a second configuration using the sleeve 154. For example, in the first configuration, the system 300 may include the instrument 100 described above, i.e. the arms 102 and 104 and the reducer 112 with the reduction tube 114 and associated handle 116 and be used to compressor, distract, and reduce as described above.

Figure 12:
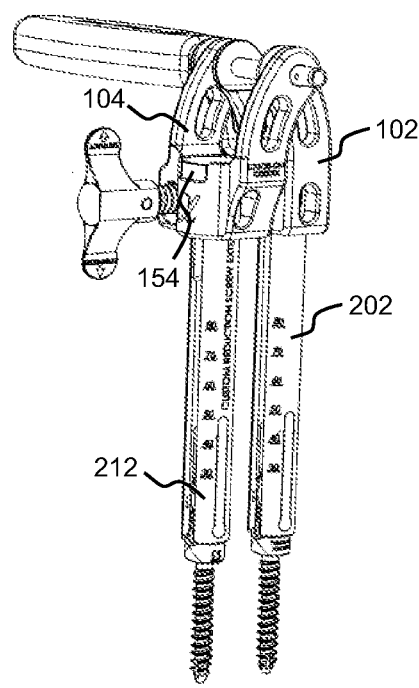
FIG. 12 illustrates the system of FIG. 11 in an exemplary configuration for compression and distraction of a vertebral segment according to the principles of the present disclosure.

In the second configuration, illustrated in FIGS. 12-14, the system may include arms 102 and 104 with the sleeve 154 and be used to compress and distract. The sleeve 154 includes an outer diameter D4 corresponding to the second diameter D2 of the second aperture 134 and an inner diameter corresponding to the outer diameter D3 of the second extender 212. The sleeve 150 may be inserted into the second aperture 134 in place of the reduction tube 132. Various attachment features may rigidly attach or couple the sleeve 154 within the aperture and provide the same coupling with the second extender 212 as the first aperture 132 provides with the first extender 202.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An instrument for compression and distraction of a vertebral segment and reducing a surgical rod, comprising:
a first arm including a first aperture for receiving a first screw extender that attaches to a first vertebra;
a second arm pivotably coupled to the first arm and including a second aperture for receiving a second screw extender that attaches to a second vertebra;
a coupler that links the first arm to the second arm to position the first arm relative to the second arm for compression and distraction of the first vertebra relative to the second vertebra; and
a reducer received within the second aperture for reducing a surgical rod within the second screw extender,
wherein the first aperture includes a first diameter and the second aperture includes a second diameter greater than the first diameter, the second diameter configured to receive the reducer.

2. The instrument of claim 1, further comprising a pivot pin that links proximal ends of the first arm and the second arm.

3. The instrument of claim 1, further comprising coupler apertures in distal ends of the first arm and the second arm for receiving the coupler.

4. The instrument of claim 1, wherein the coupler includes a first thread for engagement with the first arm and a second thread for engagement with the second arm.

5. The instrument of claim 1, further comprising pivot collars within distal ends of the first and second arms for pivotally linking the coupler with the first arm and the second arm.

6. A system for one or more surgical procedures, comprising:
a first arm including a first aperture for coupling with a first screw extender that attaches to a first vertebra;
a second arm pivotably coupled to the first arm and including a second aperture having a first configuration and a second configuration;
a removable sleeve for the second aperture in the first configuration for coupling with a second screw extender that attaches to a second vertebra;
a reducer for the second aperture in the second configuration to reduce a surgical rod within the second screw extender; and
a coupler that positions the first arm relative to the second arm for compression and distraction of the first vertebra relative to the second vertebra in the first and second configurations,
wherein the first aperture includes a first diameter and the second aperture includes a second diameter greater than the first diameter, the second diameter configured to receive one of the removable sleeve and the reducer.

7. The system of claim 6, further comprising a pivot pin that links proximal ends of the first arm and the second arm.

8. The system of claim 6, further comprising coupler apertures in distal ends of the first arm and the second arm for receiving the coupler.

9. The system of claim 6, wherein the coupler includes a first thread for engagement with the first arm and a second thread for engagement with the second arm.

10. The system of claim 6, further comprising rotatable links within distal ends of the first and second arms for rotatably coupling the coupler with the first arm and the second arm.

* * * * *